United States Patent [19]

Brown et al.

US005770608A

[11] Patent Number: 5,770,608
[45] Date of Patent: Jun. 23, 1998

[54] HETEROCYCLIC DERIVATIVES

[75] Inventors: George Robert Brown; Keith Blakeney Mallion, both of Cheshire; Peter John Harrison, deceased, late of Cheshire, all of England, by Alison Harrison, executor

[73] Assignee: Imperial Chemical Industries PLC, London, United Kingdom

[21] Appl. No.: 805,231

[22] Filed: Feb. 24, 1997

Related U.S. Application Data

[63] Continuation of Ser. No. 256,123, Jun. 23, 1994, Pat. No. 5,654,315.

[30] Foreign Application Priority Data

Dec. 23, 1991 [GB] United Kingdom .................... 9127279

[51] Int. Cl.$^6$ .......................... A01N 43/90; C07D 453/02
[52] U.S. Cl. .......................... 514/305; 514/210; 546/133; 546/136; 546/137
[58] Field of Search .................................... 514/277, 279, 514/576, 305, 210; 546/733, 136, 137

[56] References Cited

U.S. PATENT DOCUMENTS

| | | | |
|---|---|---|---|
| 3,405,134 | 10/1968 | Judd ...................................... | 260/294.3 |
| 3,534,053 | 10/1970 | Sallay et al. ......................... | 260/294.7 |
| 3,586,694 | 6/1971 | Shen et al. ........................... | 260/309.2 |
| 3,655,675 | 4/1972 | Carabateas ......................... | 260/293.74 |
| 3,679,690 | 7/1972 | Carabateas ............................. | 546/309 |
| 3,725,410 | 4/1973 | Potoski et al. .......................... | 544/362 |
| 3,763,168 | 10/1973 | Carabateas ......................... | 250/293.53 |
| 3,857,848 | 12/1974 | Mauvemay et al. .................... | 546/133 |
| 4,038,402 | 7/1977 | Kaminka et al. ....................... | 514/305 |
| 4,599,344 | 7/1986 | Morgan .................................. | 514/305 |
| 5,135,935 | 8/1992 | Alberts et al. .......................... | 514/305 |
| 5,242,914 | 9/1993 | Kawamoto et al. .................... | 514/210 |
| 5,286,864 | 2/1994 | Walther et al. ......................... | 546/137 |
| 5,385,912 | 1/1995 | Neuenschwander et al. ......... | 514/305 |
| 5,494,918 | 2/1996 | Neuenschwander et al. ......... | 514/305 |

FOREIGN PATENT DOCUMENTS

| | | |
|---|---|---|
| 77130/91 | 11/1991 | Australia . |
| 1014958 | 8/1977 | Canada . |
| 0 307 142 | 3/1989 | European Pat. Off. . |
| 0 316 718 | 5/1989 | European Pat. Off. . |
| 0 322 182 | 6/1989 | European Pat. Off. . |
| 0 328 200 | 8/1989 | European Pat. Off. . |
| 0 330 826 | 9/1989 | European Pat. Off. . |
| 0 337 637 | 10/1989 | European Pat. Off. . |
| 0 370 415 | 5/1990 | European Pat. Off. . |
| 0 412 797 | 2/1991 | European Pat. Off. . |
| 0 458 214 | 11/1991 | European Pat. Off. . |
| 0 497 415 | 8/1992 | European Pat. Off. . |
| 1 416 958 | 12/1975 | United Kingdom . |
| 2 169 292 | 7/1986 | United Kingdom . |
| 92/15579 | 9/1992 | WIPO . |
| 93/15073 | 8/1993 | WIPO . |

OTHER PUBLICATIONS

Ricciardi et al. "Facile synthesis of styrylquinuclidines" Heterocycles, vol. 24, No. 4, pp. 971–977, 1986.
Warawa et al., Quinuclidine Chemistry2. $^1$Synthesis and Antiinflammatory Properties of 2–Substituted Benzhydryl–3–quinuclidinols, J. Med. Chem., 17(5), (1974), 497–501.
Sterling et al., Quaternary and Tertiary Quinuclidine Derivatives as Inhibitors of Choline Uptake, J. Pharm. Sciences, 80(8), (1991), 785–789.
Saunders et al., Novel Quinuclidine–Based Ligands for the Muscarinic Cholinergic Receptor J. Med. Chem. 33(4), (1990), 1128–1137.
Turchin et al., Stereochemistry of Quinuclidines Containing a Substituent with Aryl (Heteroaryl) Nuclei at Position Three, Khimiko–farmatsevitcheskii Zhurnal, 1986, vol. 20, pp. 65–72.
WO,A,9215 579, Sep. 17,1992, pp.36 and 37—claims.

Primary Examiner—Ardin H. Marschel
Assistant Examiner—Jezia Riley
Attorney, Agent, or Firm—Cushman Darby & Cushman Intellectual Property Group of Pillsbury Madison & Sutro, LLP

[57] ABSTRACT

Quinuclidine compounds of the formula I:

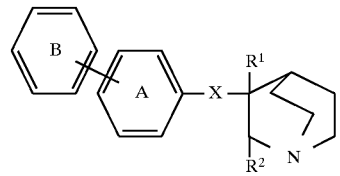

$R^1$ is hydrogen or hydroxy;
$R^2$ is hydrogen;
or $R^1$ and $R^2$ are joined together so that $CR^1$—$CR^2$ is a double bond;
X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —CH=N—, —N=CH—, —$CH_2S$—, —$SCH_2$—, wherein the sulphur atom in the latter two groups may optionally bear one or two oxygen atoms; and
wherein one or both of ring A and ring B may be optionally unsubstituted or independently substituted by one or more substituents selected from halogeno, hydroxy, amino, nitro, cyano, carboxy, carbamoyl, alkyl, alkenyl, alkoxy, alkylamino, di-alkyl]amino, N-alkyl]carbamoyl, N,N-di-alkyl]carbamoyl, alkoxycarbonyl, alkylthio, alkylsulphinyl, alkylsulphonyl and halogeno-alkyl; are inhibitors of squalene synthase and are hence useful in treating diseases or medical conditions such as hypercholesterolemia, atherosclerosis and fungal diseases. Methods of using these compounds to treat such conditions, novel compounds, processes for making these compounds and pharmaceutical compositions containing them are claimed.

9 Claims, No Drawings

HETEROCYCLIC DERIVATIVES

This is a continuation of application Ser. No. 08/256,123, filed Jun. 23, 1994 now U.S. Pat. No. 5,654,315.

FIELD OF INVENTION

This invention relates to novel heterocyclic derivatives and, more particularly to novel heterocyclic derivatives which possess the pharmacologically useful property of inhibiting squalene synthase. The invention also relates to pharmaceutical compositions for use in treating diseases or medical conditions such as hypercholesterolemia and atherosclerosis, as well as other diseases and conditions in which inhibition of squalene synthase is desirable. The invention also relates to processes for the preparation of the novel heterocyclic derivatives, and to their use in medicine.

BACKGROUND

Several different classes of compounds have been reported to possess the capability of being able to lower cholesterol levels in blood plasma. For example agents which inhibit the enzyme HMG CoA reductase, which is essential for the production of cholesterol, have been reported to reduce levels of serum cholesterol. Illustrative of this class of compounds is the HMG CoA reductase inhibitor known as lovastatin which is disclosed in U.S. Pat. No. 4,231,938. Other agents which are reported to lower serum cholesterol include those which act by complexing with bile acids in the intestinal system and which are hence termed "bile acid sequestrants". It is believed that many of such agents act by sequestering bile acids within the intestinal tract. This results in a lowering of the levels of bile acid circulating in the enteroheptatic system and promoting replacement of bile acids by synthesis in the liver from cholesterol, which synthesis results, inter alia, in a lowering of circulating blood cholesterol levels.

Squalene synthase is a microsomal enzyme which catalyses the first committed step of cholesterol biosynthesis. Two molecules of farnesyl pyrophosphate (FPP) are condensed in the presence of the reduced form of nicotinamide adenine dinucleotide phosphate (NADPH) to form squalene. The inhibition of this committed step to cholesterol should leave unhindered biosynthetic pathways to ubiquinone, dolichol and isopentenyl t-RNA. Elevated cholesterol levels are known to be one of the main risk factors for ischaemic cardiovascular disease. Thus, an agent which inhibits squalene synthase should be useful in treating diseases and medical conditions in which a reduction in the level of cholesterol is desirable, for example hypercholesterolemia and atherosclerosis.

Thus far, the design of squalene synthase inhibitors has concentrated on the preparation of analogues of the substrate farnesyl pyrophosphate (FPP), and hence on compounds which contain phosphorus groups. For example, the preparation of phosphorous-containing squalene synthase inhibitors is reported in published European Patent Application No. 409,181; and the preparation of isoprenoid (phosphinylmethyl)phosphonates as inhibitors of squalene synthase is reported by Biller et al, J. Med. Chem., 1988, 31, 1869.

Certain quinuclidine derivatives are reported in EP 458, 214 to be muscarinic agonists.

SUMMARY OF INVENTION

The present invention is based on the discovery that certain heterocyclic derivatives are inhibitors of squalene synthase, and are hence useful in treating diseases and medical conditions in which inhibition of squalene synthase is desirable.

According to the present invention there is provided a compound of formula I (formula set out hereinafter together with the other chemical formulae referred to herein), or a pharmaceutically acceptable salt thereof, wherein:
$R^1$ is hydrogen or hydroxy;
$R^2$ is hydrogen;
or $R^1$ and $R^2$ are joined together so that $CR^1$ —$CR^2$ is a double bond;
X is selected from —$CH_2CH_2$—, —CH=CH—, —C≡C—, —$CH_2O$—, —$OCH_2$—, —$CH_2NH$—, —$NHCH_2$—, —$CH_2CO$—, —$COCH_2$—, —CH=N—, —N=CH—, —$CH_2S$—, —$SCH_2$—, wherein the sulphur atom in the latter two groups may optionally bear one or two oxygen atoms; and
wherein one or both of ring A and ring B may be optionally unsubstituted or independently substituted by one or more substituents selected from halogeno, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl and halogeno–(1–6C)alkyl; provided that when X is selected from —$CH_2NH$—, —CH=N—, —$CH_2O$— and —$CH_2S$— (optionally bearing one or two oxygen atoms), $R^1$ is not hydroxy.

It will be appreciated that, depending on the nature of the substituents, certain of the compounds of formula I may possess one or more chiral centres. In such circumstances, it will be appreciated that the compounds of the invention may exist in, and be isolated in, optically active or racemic form. The invention includes any optically active or racemic form of a compound of formula I which possesses the beneficial pharmacological effect of inhibiting squalene synthase. The synthesis of optically active forms may be carried out by standard techniques of organic chemistry well known in the art, for example by, resolution of a racemic form, by synthesis from optically active starting materials or by asymmetric synthesis.

It is also to be understood that generic terms such as "alkyl" include both the straight chain and branched chain groups such as butyl and tert-butyl. However, when a specific term such as "butyl" is used, it is specific for the straight chain or "normal" butyl group, branched chain isomers such as "t-butyl" being referred to specifically when intended.

It will be appreciated that when $R^1$ and $R^2$ are joined so that $CR^1$ —$CR^2$ is a double bond, the heterocyclic ring in formula I will comprise the 2,3-dehydroquinuclidine moiety shown in formula Ia.

A particular value for an alkyl substituent which may be present on ring A or ring B is, for example, (1–4C)alkyl, such as methyl, ethyl, propyl, isopropyl, butyl, isobutyl or sec-butyl.

A particular value for an alkenyl substituent which may be present on ring A or ring B is, for example, (2–4C)alkenyl, such as allyl, but-2-enyl or 2-methyl-2-propenyl.

A particular value for alkoxy substituent which may be present on ring A or ring B is, for example, (1–4C)alkoxy; such as methoxy, ethoxy, propoxy, isopropoxy or butoxy.

A particular value for an alkylamino substituent which may be present on ring A or ring B is, for example, (1–4C)alkylamino, such as methylamino, ethylamino, propylamino or butylamino.

A particular value for a di-alkylamino substituent which may be present on ring A or ring B is, for example, dimethylamino, diethylamino, methylpropylamino or dipropylamino.

A particular value for an alkylcarbamoyl substituent which may be present on ring A or ring B is, for example, N-methylcarbamoyl, N-ethylcarbamoyl or N-propylcarbamoyl.

A particular value for a di-alkylcarbamoyl substituent which may be present on ring A or ring B is, for example, N,N-dimethylcarbamoyl or N,N-diethylcarbamoyl.

A particular value for an alkoxycarbonyl substituent which may be present on ring A or ring B is, for example, methoxycarbonyl, ethoxycarbonyl or propoxycarbonyl.

A particular value for an alkylthio substituent which may be present on ring A or ring B is, for example, methylthio, ethylthio, propylthio, isopropylthio or butylthio.

A particular value for an alkylsulphinyl substituent which may be present on ring A or ring B is, for example, methylsulphinyl, ethylsulphinyl, propylsulphinyl, isopropylsulphinyl or butylsulphinyl.

A particular value for an alkylsulphonyl substituent which may be present on ring A or ring B is, for example, methylsulphonyl, ethylsulphonyl, propylsulphonyl, isopropylsulphonyl or butylsulphonyl.

A particular value for a halogeno substituent which may be present on ring A or ring B is, for example, fluoro, chloro or bromo.

A particular value for halogenoalkyl substituent which may be present on ring A or ring B is, for example, one which contains one, two or three halo groups selected from fluoro, chloro and bromo and the alkyl group is selected from methyl, ethyl, propyl, iso-propyl, butyl, isobutyl or sec-butyl, especially trifluoromethyl.

The ring B may be attached to ring A so that ring B is ortho-, meta- or para- to the group X. Thus, ring A may comprise a 1,4-phenylene, 1,3-phenylene or a 1,2-phenylene moiety. In general it is preferred, for example, that ring B is meta or para to the group X, especially para. Thus in general it is preferred, for example, that ring A is a 1,4-phenylene or a 1,3-phenylene moiety, especially a 1,4-phenylene moiety.

In general it is preferred, for example, that one or both of ring A or ring B is independently unsubstituted or substituted by one or more substituents selected from halogeno, hydroxy, nitro, cyano, (1–6C)alkyl, (2–6C)alkenyl, (1–6C)alkoxy, (1–6C)alkylthio, (1–6C)alkylsulphinyl, (1–6C)alkylsulphonyl and halogeno-(1–6C)alkyl.

In general, it is preferred that, ring A and ring B may be unsubstituted or may bear up to three substituents in total. For example, ring A may be unsubstituted, with ring B bearing up to three substituents; or ring A may bear a single substituent and ring B bear up to two substituents.

In a specific example, ring A and ring B are both unsubstituted. In a further specific example, ring A is unsubstituted 1,4-phenylene moiety and ring B is optionally substituted by one, two or three substituents selected from halogeno, hydroxy, nitro, cyano, (1–6C)alkyl, (2–6C)alkenyl, (1–6C)alkoxy, (1–6C)alkylthio, (1–6C)alkylsulphinyl, (1–6C)alkylsulphonyl and halogeno-(1–6C)alkyl.

A particular value for X is one selected from the group: —$CH_2CH_2$—, —CH═CH—, —C≡C—, —$CH_2O$—, —$OCH_2$—, —$CH_2NH$—, —$NHCH_2$—, —$CH_2CO$—, —$COCH_2$—, —$CH_2S$—, —$SCH_2$—, wherein the sulphur atom in the latter two groups may optionally bear one or two oxygen atoms.

A more particular value for X is one selected from the group: —$CH_2CH_2$—, —CH═CH—, —C≡C—, —$OCH_2$—, —$CH_2CO$—, —$COCH_2$—, and —$SCH_2$ wherein the latter group may optionally bear one or two oxygen atoms.

A more particular value for X is —$CH_2CH_2$—, —CH═CH—, —C≡C—, —$CH_2NH$—, —$NHCH_2$—, —$CH_2CO$—or —$COCH_2$—.

A further group of values of X of interest is —$CH_2CH_2$—, —CH═CH—, —C≡C—, —$CH_2CO$— and —$COCH_2$—.

Values of X of particular interest include —$CH_2CH_2$—, —CH═CH— and —C≡C—, especially —CH═CH— and —C≡C—.

Particular values for ring A and ring B include those in which ring A is an unsubstituted 1,4-phenylene moeity and ring B is unsubstituted or bears one two or three substituents selected from alkoxy (such as methoxy or ethoxy), hydroxy and halogeno (such as fluoro or chloro).

In one embodiment of the present invention, $R^1$ and $R^2$ are both hydrogen, and the other radicals are as defined above; in a second embodiment, $R^1$ is hydroxy and $R^2$ is hydrogen, and the other radicals are as defined above; and in a further embodiment $R^1$ and $R^2$ are joined together so that $CR^1$—$CR^2$ is a double bond, and the other radicals are as defined above.

In a further embodiment, when X is selected from —$CH_2N$—, —CH═N—, —$CH_2O$— and —$CH_2S$— (optionally bearing one or two oxygen atoms), $R^1$ and $R^2$ are both hydrogen.

In a particular embodiment of the present invention there is provided a compound of formula I, or a pharmaceutically acceptable salt thereof, wherein:

$R^1$ is hydrogen or hydroxy; $R^2$ is hydrogen; or $R^1$ and $R^2$ are joined together so that $CR^1$ –$CR^2$ is a double bond; X is selected from —$CH_2CH_2$—, —CH═CH—, —C≡C—, —$CH_2O$—, —$OCH_2$—, $CH_2NH$—, —$CH_2NH$—, —$CH_2CO$—, —$COCH_2$—, —$CH_2S$—, —$SCH_2$—, wherein the sulphur atom in the latter two groups may optionally bear one or two oxygen atoms; and
wherein one or both of ring A and ring B may be optionally unsubstituted or independently substituted by one or more substituents selected from halogeno, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl and halogeno-(1–6C)alkyl;
provided that when X is selected from —$CH_2NH$—, —CH═N—, —$CH_2O$— and —$CH_2S$— (optionally bearing one or two oxygen atoms), $R^1$ is not hydroxy.

Particular and preferred values for the various groups are the appropriate values mentioned above.

In a further embodiment of the present invention there is provided a compound of formula I, or a pharmaceutically acceptable salt thereof, wherein:
$R^1$ is hydrogen or hydroxy; $R^2$ is hydrogen; or $R^2$ and $R^1$ are joined together so that $CR^1$ —$CR^2$ is a double bond; X is selected from —$CH_2CH_2$—, —CH═CH—, —$OCH_2$—, —$COCH_2$—, and —$SCH_2$—, wherein the latter group may optionally bear one or two oxygen atoms; wherein one or both of ring A and ring B may optionally be unsubstituted or substituted by one or more substituents selected from halogeno, hydroxy, nitro, (1–6C)alkyl, (2–6C)alkenyl, (1–6C)alkoxy, (1–6C)alkylthio, (1–6C)alkylsulphinyl, (1–6C)alkylsulphonyl and halogeno-(1–6C)alkyl.

Particular and preferred values for the various groups are the appropriate values mentioned above.

In a further embodiment of the present invention there is provided a compound of formula I, or a pharmaceutically acceptable salt thereof, wherein:
$R^1$ is hydrogen or hydroxy; $R^2$ is hydrogen; or $R^1$ and $R^2$ are joined together so that $CR^1$—$CR^2$ is a double bond; X is selected from —$CH_2CH_2$—, —CH═CH—, —C≡C—, —$CH_2O$—, —$OCH_2$—, —$CH_2NH$—, —$CH_2NH$—, —CH$_2$CO—, —COCH$_2$—, —CH$_2$S—, —SCH$_2$—, wherein the sulphur atom in the latter two groups may optionally bear one or two oxygen atoms; ring B is para to the group X; and wherein one or both of ring A and ring B may be optionally unsubstituted or independently substituted by one or more substituents selected from halogeno, hydroxy, amino, nitro, cyano, carboxy, carbamoyl, (1–6C) alkyl, (2–6C)alkenyl, (1–6C)alkoxy, (1–6C)alkylamino, di[(1–6C)alkyl]amino, N-[(1–6C)alkyl]carbamoyl, N,N-di-[(1–6C)alkyl]carbamoyl, (1–6C)alkoxycarbonyl, (1–6C) alkylthio, (1–6C)alkylsulphinyl, (1–6C)alkylsulphonyl and halogeno-(1–6C)alkyl; provided that when X is selected from —CH$_2$NH—, —CH$_2$O— and —CH$_2$S— (optionally bearing one or two oxygen atoms), R$^1$ is not hydroxy.

Particular and preferred values for the various groups are the appropriate values mentioned above.

In a further embodiment there is provided a compound of formula I, or a pharmaceutically acceptable salt thereof, wherein: R$^1$ is hydroxy; R$^2$ is hydrogen; or R$^1$ and R$^2$ are joined together so that CR$^1$—CR$^2$ is a double bond;
X is selected from —CH$_2$CH$_2$—, —CH=CH—, —C≡C—, —CH$^2$O—, —OCH$_2$—, —CH$_2$NH—, —NHCH$_2$—, —CH$_2$CO—, —COCH$_2$—, —CH=N—, —N=CH—, —CH$_2$S—, —SCH$_2$—, wherein the sulphur atom in the latter two groups may optionally bear one or two oxygen atoms; and wherein one or both of ring A and ring B may be optionally unsubstituted or independently substituted by one or more substituents selected from halogeno, hydroxy, amino, nitro, cyano, carboxy, carbamoyl, (1–6C) alkyl, (2–6C)alkenyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C) alkylthio, (1–6C)alkylsulphinyl, (1–6C)alkylsulphonyl and halogeno-(1–6C)alkyl; provided that when X is selected from —CH$_2$NH—, —CH=N—, —CH$_2$O— and —CH$_2$S— (optionally bearing one or two oxygen atoms), R$^1$ is not hydroxy.

Particular and preferred values for the various groups are the appropriate values mentioned above.

In a further embodimemt there is provided a compound of formula I,or a pharmaceutically acceptable salt thereof, wherein:
R$^1$ is hydroxy; R$^2$ is hydrogen; X is selected from —CH$_2$CH$_2$—, —CH=CH—, —C≡C—, —OCH$_2$—, —NHCH$_2$—, —CH$_2$CO—, —COCH$_2$—, —N=CH—, —SCH$_2$—, wherein the sulphur atom in the latter groups may optionally bear one or two oxygen atoms; ring A is a 1,4-phenylene moeity; and wherein one or both of ring A and ring B may be optionally unsubstituted or independently substituted by one or more substituents selected from halogeno, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl and halogeno-(1–6C)alkyl.

Particular and preferred values for the various groups are the appropriate values mentioned above.

In a further embodiment R$^1$ is hydrogen or hydroxy; R$^2$ is hydrogen;
or R$^1$ and R$^2$ are joined together so that CR$^1$ —CR$^2$ is a double bond;
X is selected from —CH$_2$CH$_2$—, —CH=CH—, —CEC—, —CH$_2$NH—, —NHCH$_2$—, —CH$_2$CO—and —COCH$_2$—; ring A is a 1,4-phenylene moiety; and
wherein one or both of ring A and ring B may be optionally unsubstituted or independently substituted by one or more substituents selected from halogeno, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-[(1–6C)alkyl]carbamoyl, N,N-di-[(1–6C)alkyl] carbamoyl, (1–6C)alkoxycarbonyl, (1–6C)alkylthio, (1–6C) alkylsulphinyl, (1–6C)alkylsulphonyl and halogeno-(1–6C) alkyl; provided that when X is —CH$_2$NH—, R$^1$ is not hydroxy.

In an embodiment of particular interest R$^1$ is hydroxy; R$^2$ is hydrogen; X is —C≡C—; ring A is a 1,4-phenylene moeity; and wherein one or both of ring A and ring B may be optionally unsubstituted or independently substituted by one or more substituents selected from halogeno, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C) alkylthio, (1–6C)alkylsulphinyl, (1–6C)alkylsulphonyl and halogeno-(1–6C)alkyl.

Particular and preferred values for the various groups are the appropriate values mentioned above.

In a further embodiment of interest R$^1$ is hydrogen; R$^2$ is hydrogen; X is selected from —CH$_2$CH$_2$—, —CH=CH—, —C≡C—, —CH$_2$NH—, —CH$_2$CO—, —COCH$_2$—; ring A is a 1,4-phenylene moeity; and wherein one or both of ring A and ring B may be optionally unsubstituted or independently substituted by one or more substituents selected from halogeno, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-[(1–6C)alkyl] carbamoyl, N,N-di-[(1–6C)alkyl]carbamoyl, (1–6C) alkoxycarbonyl, (1–6C)alkylthio, (1–6C)alkylsulphinyl, (1–6C)alkylsulphonyl and halogeno-(1–6C)alkyl.

Particular and preferred values for the various groups are the appropriate values mentioned above.

In a further embodiment of particular interest R$^1$ is hydrogen or hydroxy; R$^2$ is hydrogen; or R and R$^2$ are joined together so that R$^1$—CR$^2$ is a double bond; X is selected from —CH$_2$CH$_2$—, —CH=CH—, —OCH$_2$—, —SCH$_2$—, and —COCH$_2$—; and ring A and ring B are both unsubstituted.

As mentioned above, it is generally preferred that ring B is para to the group X.

Compounds of the invention which are of particular interest include the compounds described in the accompanying Examples (and their pharmaceutically-acceptable salts), and are hence provided as a further feature of the present invention.

A suitable pharmaceutically-acceptable salt of the present invention comprises an acid-addition salt derived from an inorganic or organic acid which provides a pharmaceutically-acceptable anion. Thus, examples of salts of the present invention include acid-addition salts with hydrochloric, hydrobromic, nitric, sulphuric, phosphoric, trifluoroacetic, citric, tartaric, succinic, maleic, fumaric or acetic acid. In addition, suitable pharmaceutically-acceptable salts include [where the compound of formula I is sufficiently acidic, for example where the compound of formula I bears an acidic substituent such as carboxy]those formed with a base which affords a pharmaceutically acceptable cation. Suitable bases include an alkali metal salt (such as a sodium or potassium salt), an alkaline earth metal salt (such as a calcium or magnesium salt), an ammonium salt or a salt with an organic base which affords a physiologically-acceptable cation such as a salt with methylamine, dimethylamine, triethylamine, piperidine or morpholine.

The compounds of the present invention may be obtained by standard procedures of organic chemistry already known to be applicable to the preparation of structurally analogous compounds. Such procedures for the preparation of the compounds of formula I, or pharmaceutically acceptable salts thereof, are provided as a further feature of the present invention and are illustrated by the following preferred processes in which the various generic radicals, for example, $R^1$, $R^2$ and X may take any of the meanings hereinbefore defined, and in which the rings A and B may optionally be unsubstituted or substituted as hereinbefore defined.

Thus, according to the present invention there is also provided a process for preparing a compound of formula I, or a pharmaceutically-acceptable salt thereof, which process comprises:

(a) For those compounds of formula I in which $R^1$ and $R^2$ are both hydrogen, reducing a compound of formula I in which $R^1$ and $R^2$ are joined together so that $CR^1$—$CR^2$ is a double bond (provided that X is not —C≡C— or —CH=CH—).

The reduction may be carried out, for example, by catalytic hydrogenation, or by reaction with a suitable reducing agent. Suitable reaction conditions include, for example, catalytic hydrogenation using a catalyst which comprises a noble metal. Particular catalysts include palladium, platinum and nickel (especially when in the finely divided state known as raney nickel), and catalysts in which the noble metal is supported on an inert carrier such as carbon. A specific example of a supported catalyst is Pd/C. The reduction is conveniently carried out in a solvent of, for example, an alcohol such as ethanol, and at (or near) ambient temperature and optionally under pressure.

Further suitable reaction conditions include, for example, reduction with a borane such as diborane. The reaction is generally carried out in an inert solvent of, for example, tetrahydrofuran or methyl t-butyl ether at, for example, 0–60° C. It may be preferable to cool the reaction below ambient temperature (eg. to about 0° C.) during the reduction. The borane generated may be hydrolysed by treatment with an organic acid such as acetic acid, which hydrolysis may be carried out at 0–60° C., and may be accelerated by heating (eg. refluxing).

(b) For compounds of formula I in which $R^1$ and $R^2$ are joined together so that $R^1$—$CR^2$ is a double bond, dehydrating a compound of formula I in which $R^1$ is hydroxy and $R^2$ is hydrogen.

The dehydration may be carried out using an acid such as sulphuric acid (eg. concentrated sulphuric acid), or p-toluene sulphonic acid. The reaction is conveniently carried out with heating, and conveniently an inert solvent is employed. For example, the reaction may be carried out using sulphuric acid at temperatures of about 70–130° C.; or using p-toluene sulphonic acid in a hydrocarbon solvent of, for example, toluene or xylene at ambient temperature to reflux, and preferably at reflux. The dehydration may also be carried out using trifluoroacetic acid in an inert solvent such as dichloromethane (at ambient temperature to reflux temperature).

(c) For compounds of formula I in which $R^1$ and $R^2$ are joined together so that $R^1$—$CR^2$ is a double bond, treating a compound of formula II in which Z is a leaving group with a base.

Suitable values for Z include, for example, halogen such as chloro, bromo, iodo, or a methylsulphonyloxy or toluenesulphonyloxy group. Suitable bases include hydroxide (such as potassium or sodium hydroxide), and alkoxide (such as potassium t-butoxide or sodium ethoxide).

The reaction is conveniently carried out in the presence of a solvent, preferably a polar organic solvent. Suitable solvents include, for example, an alcohol (such as ethanol), or an aprotic solvent such as dimethylformamide or N-methylpyrrolidone. The reaction may be carried out at ambient temperature or at an elevated temperature, such as at a temperature between ambient and the reflux temperature of the reaction mixture. This method is generally preferred over that described in (b) when X is —$OCH_2$— or —$SCH_2$—.

The compounds of formula II may be prepared from a compound of formula I in which $R^1$ is hydroxy. For example, where Z is halogen the compound of formula I in which $R^1$ is hydroxy and $R^2$ is hydrogen may be reacted with the appropriate phosphorous halide (eg. $PCl_5$, $PBr_3$ or $PI_3$), or where Z is chloro, by reaction with thionyl chloride. The compound of formula I in which $R^1$ is hydroxy may be reacted with mesyl chloride to the compound in which Z is methylsulphonyloxy; and with tosyl chloride to give Z is toluene sulphonyloxy.

(d) For those compounds of formula I in which X is —$COCH_2$—, reacting an organometallic compound of formula III in which M is a metal atom or a derivative thereof, with a compound of formula IV.

Suitable values for H include, for example, magnesium and lithium. In the case where M is magnesium it is conveniently present in the form of a derivative of formula —MgX where X is a halogen atom such as iodo or bromo, so that the organometallic compound of formula III is in the form known as a Grignard Reagent. The reaction is generally carried out in an inert solvent such as dry diethyl ether or tetrahydrofuran, with cooling. For example, the reaction may be carried out at a temperature below 0° C., such as at a temperature between 0°C. and −78° C.

The compounds of formula III may be prepared from a compound of formula IIIa in which "hal" is a halogen atom, such as iodo or bromo. The compound of formula IIIa may be reacted directly with the metal M. Thus in the case of magnesium, the Grignard Reagent of formula III may be prepared by reaction of a compound of formula IIIa in which "hall" is bromo or iodo with magnesium turnings in an inert solvent such as diethyl ether, as is well known in the art. Where M is lithium, the compound of formula III may be prepared by reaction of the compound of formula IIIa with lithium in an inert solvent such as diethyl ether, or by reaction with an alkyl lithium derivative such as sec-butyl lithium in an inert solvent such as diethyl ether or tetrahydrofuran, as is well known in the art.

e) For compounds of formula I in which X is —CH=N—, reacting a compound of formula V with a compound of formula VI.

The reaction is generally carried out in an inert hydrocarbon solvent such as toluene or benzene, with heating (eg. at reflux). The reaction may be accelerated by removing water generated in the reaction by azeotropic distillation.

f) For those compounds of formula I in which X is —$CH_2$—NH— or —$NHCH_2$—, reducing a compound of formula I in which X is —CH=N— or —N=CH— (as appropriate).

The reaction may be carried out using a chemical reducing agent such as a hydride in a solvent such as an alcohol at ambient temperature. Thus, in a particular example, the reduction may be carried out using sodium borohydride in a solvent of methanol at ambient temperature. The reduction may also be carried out by catalytic hydrogenation using similar conditions to those described under (a) above.

The preferred method of reduction will depend upon the nature of substituents on rings A and B and the value of X. Thus, for example, where debenzylation is possible (eg. when X is —$CH_2NH$—), it is generally preferred that a chemical reducing agent is employed.

g) For those compounds of formula I in which X is —NHCH$_2$—, —OCH$_2$—, —SCH$_2$, R$^1$ is hydroxy and R$^2$ is hydrogen, reacting a compound of formula VII in which Z is —NH$^2$—, —OH or SH as appropriate with a compound of formula VIII.

The reaction is conveniently carried out in a solvent such an inert hydrocarbon eg. toluene with heating. The reaction may be facilitated by the presence of acid or base.

The compound of formula VIII is conveniently generated in situ, as described in Example 6 below.

The compound of formula VIII may also be prepared from a "halohydrin" as is well known in the art. The halohydrin may be prepared by oxidation of the corresponding olefin using, for example HOCl and the halohydrin treated with base (eg. NaOH) to give the compound of formula VIII.

h) For compounds of formula I in which X is —CH═CH—, reacting a compound of formula IX with a compound of formula X in the presence of a base.

Suitable bases include alkoxides, such as potassium t-butoxide, and the reaction is conveniently carried out in an inert solvent such as tetrahydrofuran with cooling below ambient temperature eg −40° C. to 0°C.).

The compounds of formula IX may be prepared by reaction of a compound of formula IXa in which W is a halogen, such as chloro, with triphenylphosphine. Suitable conditions are those mentioned in Example 2a below.

i) For those compounds of formula I in which X is —CH$^2$CH$^2$—, reducing a compound of formula I in which X is —CH═CH— or —C≡C—.

The reaction may conveniently be carried out by catalytic hydrogenation using conditions similar to those mentioned in (a) above.

In an alternative synthesis a compound of formula ARCH$_2$CH$_2$hal wherein Ar represents the biphenyl moiety containing, rings A and B and hal represents a halogen such as bromo, is reacted with quinuclidin-3-one in the presence of sec-butyl lithium, with cooling (eg −70°C.) in an inert solvent such as tetrahydrofuran.

j) For compounds of formula I in which X is —CH$_2$CO—, reacting a compound of formula XVIII in which H is a metal atom or a derivative thereof, with a compound of formula XIX.

Suitable values for H and suitable reaction conditions are those mentioned in (d) above. The compounds of formula XVIII may be prepared from the corresponding halogeno compound in a manner analogous to the preparation of compounds of formula III discussed in (d) above.

k) For those compounds of formula I in which X is —CH$_2$O— or —CH$_2$S—, reacting a compound of formula XI with a compound of formula XII; in which Z$^1$ is a leaving group and Z$^2$ is —YM, or Z$^1$ is —YM and Z$^2$ is a leaving group, and wherein Y is oxygen or sulphur (as appropriate) and M is a metal atom.

Suitable leaving groups include, for example, halogen (such as chloro, bromo or iodo), methanesulphonyloxy, toluenesulphonyloxy or trifluoromethanesulphonyloxy; and suitable metals include, for example sodium and lithium.

The process is generally performed in the presence of a suitable solvent, for example, a hydrocarbon, such as toluene or xylene, or an ether such as dioxan or tetrahydrofuran, and at a temperature in the range, for example 20–150° C.

It may be desirable to protect the quinuclidine nitrogen atom during the reaction, especially when Z$^1$ is —YM, as described in (o) below.

l) For those compounds of formula I in which X is —N═CH—, reacting a compound of formula XIV with a compound of formula X.

Suitable reaction conditions are those mentioned in (e) above.

m) For those compounds of formula I in which X is —SCH$_2$— or —CH$_2$S— wherein the sulphur atom bears one or two oxygen atoms, oxidising the corresponding compound of formula I in which X is —SCH$_2$— or —CH$_2$S—.

The compounds of formula I in which X is —SCH$_2$— may be be oxidised to these in which the sulphur atom bears an oxygen atom (that is to a "sulphoxide") using, for example an appropriate quantity of sodium periodate. Further oxidation to the compound in which the sulphur atom bears two oxygen atoms (that is a "sulphone") may be carried out using a peracid such as peracetic acid or hydrogen peroxide. The oxidation of sulphur compounds to the corresponding sulphoxides and sulphones is well known in the chemical art. Compounds of formula I in which X is —CH$_2$S— may be oxidised to the corresponding sulphoxides or sulphones in the same way.

In some cases oxidation of compounds of formula I to give a sulphone may be accompanied by some oxidation of the nitrogen atom in the quinuclidine ring to the N-oxide. In such cases the quinuclidine N-oxide moiety may be reduced back to a quinuclidine moiety without affecting the sulphone using reducing agents well known in the art, such as sulphur dioxide as is mentioned in (a) below.

n) For those compounds of formula I in which X is —OCH$_2$— or —SCH$_2$— and R$^1$ and R$^2$ are both hydrogen, reacting a compound of formula XV in which Y is oxygen or sulphur as appropriate with a compound of formula XVI in which Z is a leaving group.

Suitable leaving groups include halogen, such as chloro, bromo or iodo, methanesulphonyloxy and toluenesulphonyloxy. The reaction is generally carried out in the presence of a base such as an alkali metal hydroxide, eg sodium or potassium hydroxide, and in a solvent such as dimethylsulphoxide or dimethylformamide.

o) For compounds of formula I in which X is —CH$_2$O— or —CH$_2$S—, and R$_1$ and R$_2$ are hydrogen, reacting a compound of formula XVII in which Y is oxygen or sulphur as appropriate and Q is an protecting substituent, with a compound of formula IXa in which W is a leaving group in the presence of a base, and removing the substiuent Q.

The reaction is conveniently carried out in a polar aprotic solvent such as dimethylformamide. Suitable bases include a metal hydride such as sodium hydride.

Suitable values for Q include —BH$_3$ and oxygen. Thus the compounds of formula XVII in which Q is —BH$_3$ may be prepared by treating quinuclidin-3-ol (or the corresponding thiol) with BH$_3$.THF. Following reaction with the compound of formula XVII the —BH$_3$ substituent may be removed by treatment with an acid such as hydrochloric acid in a solvent such a acetone. The compound in which Q is oxygen may be preared by oxidation of quinuclidin-3-ol using for example 30% hydrogen peroxide. Following the reaction with the compound of formula XVII the N-oxide may be reduced using, for example sulphur dioxide, to give the conpound of formula I.

p) For those compounds of formula I in which X is —C≡C—, reacting a compound of formula I in which X is —CH═CH— with a halogen, followed by treatment with a base.

A suitable halogen is bromine and the reaction is conveniently carried out in an inert solvent such as carbon tetrachloride. Suitable bases include, for example, potassium t-butoxide. This treatment is conveniently carried out in a solvent such as THF, with heating (eg. at a temperature between ambient and about 70° C.).

q) For those compounds of formula I in which X is —C≡C—, reacting a compound of formula XIII in which M is a metal atom, with quinuclidin-3-one.

A suitable metal is lithium and suitable reaction conditions include those mentioned in (d) above.

r) For those compounds in which X is —C≡C— and $R^1$ is hydrogen or hydroxy and $R^2$ is hydrogen, reacting a compound of formula XX in which $R^1$ is hydrogen or hydroxy and $R^2$ is hydrogen with a compound of formula VII in which Z is a leaving group in the presence of a catalyst.

Suitable catalysts include, for example, transition metal complexes such as palladium or nickel complexes. Particular catalysts are palladium (II) complexes, a specific example of which is $Pd(PPh_3)_2Cl_2$. Suitable values for Z include, for examples halogen (such as chloro, bromo or iodo), methanesulphonyloxy, toluenesulphonyloxy and trifluoromethanesulphonyloxy. The reaction is generally carried out in the presence of a base, for example, an amine such as triethylamine and in a solvent such as dimethylformamide with heating (for example at 60 to 100° C.). The reaction is preferably carried out in the prersence of copper (I)iodide. Compounds of formula XX may be prepared according to Scheme 1 a and 2b.

S) For those compounds in which X is —C=C— and $R^1$ is hydrogen or hydroxy and $R^2$ is hydrogen, reacting a compound of formula XXI in which $R^1$ is hydrogen or hydroxy and $R^2$ is hydrogen with a compound of formula VII in which Z is a leaving group in the presence of a catalyst.

Suitable reaction conditions are those mentioned under (p) above. Compounds of formula XXI may be prepared according to Scheme 1b and 2a.

t) For those compounds of formula I in which X is —CH$_2$CO—, decarboxylating a compound of formula XXII.

The decarboxylation will, in general be carried out by heating the compound of formula XXII. Suitable temperatures include those from about 100° C. to about 180° C., and the reaction may be carried out in solvent. The compounds of formula XXII may be prepared by hydrolysis of a compound of formula XXIII. Suitable hydrolysis conditions include acid hydrolysis using an inorganic acid such as sulphuric acid or hydrochloric acid, conveniently at an elevated temperature. Thus it is generally preferred that the compound of formula XXIII is converted to the compound of formual I without isolation of the compound of formual XXII. Thus in particular, a compound of formula XIII may be heated at, for example 100° C. to 150° C., in sulphuric or hydrochloric acid. For example the compound of formula XIII may be heated at about 100° C. in aqueous sulphuric acid or at about 115° C. in concentrated hydrochloric acid.

The compounds of formula XXIII may be prepared by reaction of the appropriate biphenylacetonitrile with a base such as sodium hydride in an inert sovent such as xylene, followed by reaction with a quinuclidine-3-carboxylic acid ester (eg the methyl ester) at an elevated temperature such as the reflux temperature of the reaction mixture. Particularly suitable reaction conditions are those mentioned in Example 13 below. The biphenylacetonitriles may be prepared by methods well known in the art, for example, reaction of a compound of formula IX with a cyanide such as sodium cyanide in a polar aprotic solvent such as an alcohol (eg ethanol or an aqueous ethanol) at an elevated temperature (eg at the refux temperature of the reaction mixture).

(u) Reacting a compound of formula XXIV in which Z is a suitable leaving group with a compound of formula XXV in which $L^1$ and $L^2$ are suitable ligands in the presence of a catalyst.

Suitable values for Z include, for example, halogen such as bromo or iodo, and a trifluoromethanesulphonyloxy group. Suitable values for the ligands $L^1$ and $L^2$ present on the boron atom include groups independently selected from hydroxy, (1–4C)alkoxy (such as methoxy or ethoxy) and (1–6C)alkyl (such as methyl, ethyl, propyl or butyl). The groups LI and $L^2$ may, together with the boron atom to which they are attached, form a boroxin ring. The groups $L^1$ and $L^2$ may be joined together to define an -oxyalkyleneoxy- group so that $L^1$ and $L^2$ together with the boron atom define a cyclic borate ester group. A particularly suitable leaving group is the group —$B(OH)_2$.

Suitable catalysts include, for example, a catalyst selected from a palladium (0), palladium (II), nickel (0) and nickel (II) catalyst. Particular catalysts include, for example, tetrakis-(triphenylphosphine)nickel(O), bis(triphenylphosphine)nickel(II) chloride, nickel(II)chloride, palladium(II)chloride, bis(triphenylphosphine)palladium(II) chloride, bis(triphenylphosphine)phenylpalladium iodide and tetrakis(triphenylphosphine)palladium(O). A radical initiator, for example, azo(bisisobutyronitrile) may also be present.

The process is generally performed in the presence of a suitable solvent or diluent, for example, a hydrocarbon, such as toluene or xylene, or an ether such as dioxan or tetrahydrofuran, and at a temperature in the range, for example, 20–150° C.

The compounds of formula XXV may be prepared by reaction of a boron compound of formula RO—$BL^1(L^2)$ in which $L^1$ and $L^2$ are alkyl or alkoxy groups as defined above. Thus, for example, a compound of formula $B(OR)_3$ wherein R is a (1–6C)alkyl group may be reacted with a Grignard Reagent or phenyllithium compound derived, using standard procedures such as those mentioned in (d) above, from a compound of formula Ar-hal wherein "hal" represents a halogeno atom such as bromo or iodo and Ar represents ring B. The reaction is generally carried out in a solvent such as tetrahydrofuran or diethyl ether, or a mixture thereof, and at a temperature of –78° C. to 25° C. The compounds of formula XXV wherein the ligands attached to boron are alkoxy may be converted to those in which the ligands are hydroxy by hydrolysis using standard techniques. The boroxin compounds may be prepared from the latter by dehydration using standard procedures.

The compounds of formula XXV may be prepared in an analogous manner to the methods described above for the preparation of compounds of formula I.

The various starting material referred to above are known or may be prepared from known materials by techniques well known in the art. For example biphenyl derivatives may be prepared by coupling the appropriate benzene derivatives using an a catalyst. For example a catalyst of copper may be used (Ullmann reaction). Biphenyl derivatives may also be prepared by reaction of a phenylboronic acid derivative with a compound of formula Ar—X in which Ar is a phenyl ring and X is a leaving group such as bromo or triflate, in the presence of a catalyst. The reaction is analogous to that described under (u) above, where suitable reaction conditions are described.

It will be appreciated that in some of the reactions mentioned herein it may be necessary/desirable to protect any sensitive groups in the compounds. The instances where protection is necessary or desirable and suitable methods for protection are known to those skilled in the art. Thus, if reactants include groups such as amino, carboxy or hydroxy it may be desirable to protect the group in some of the reactions mentioned herein. Suitable protecting groups for hydroxy include, for example, silyl groups such as trimethylsilyl or t-butyldimethylsilyl, tetrahydropyranyl and esterifing groups such as a methyl or ethyl ester; and for amino groups include benzyloxycarbonyl and t-butoxycarbonyl. Carboxy groups may be protected in a reduced form such as in the form of the corresponding protected alcohol, which may be subsequently oxidised to give the carboxy group. The protecting groups may be removed at any convenient stage in the synthesis using conventional techniques well known in the chemical art.

It will also be appreciated that the preferred process for preparing a particular compound of formula I will depend upon the nature of the various radicals. Similarly, the preferred choice of reagent will depend upon the nature of the various radicals present. For example, when it is required to reduce a particular compound the reducing agent will generally be selected to be one which does not interfere with other groupings present.

It will also be appreciated that certain of the various optional substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acylhalide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

When a pharmaceutically-acceptable salt of a compound of the formula I is required, it may be obtained, for example, by reaction of said compound with the appropriate acid (which affords a physiologically acceptable anion), or with the appropriate base (which affords a physiologically acceptable cation), or by any other conventional salt formation procedure.

As mentioned previously, the compounds of the formula I (and their pharmaceutically-acceptable salts) are inhibitors of the enzyme squalene synthase. Thus the compounds of the present invention are capable of inhibiting cholesterol biosynthesis by inhibition of de novo squalene production.

The beneficial pharmacological properties of the compounds of the present invention may be demonstrated using one or more of the following techniques.

(a) Inhibition of Squalene synthase

In this test, the ability of a compound to prevent the formation of squalene from a radioactive substrate (tritiated farnesyl pyrophosphate) is assessed.

The test compound is incubated at a concentration of 25 micromolar in 200µl of a buffered solution containing potassium phosphate (50 mM), $HgCl_2$ (4.95 mM), KF (9.9 mM), NADPH (0.9 mM) and rat liver microsomal protein (20 pg). Rat liver microsomes are prepared by the method described in published European Patent Application No. 324,421 and stored in liquid nitrogen prior to assay. Assay vials are kept at 37° C. throughout the incubation.

The reaction is started with the addition of the substrate (1-[$^3$H]-farnesyl pyrophosphate), final concentration 20 µM, and stopped after 15 minutes reaction time with the addition of 50 µl of 4% KOH. The reaction products are separated from unreacted substrate after application to a C-18 octadecyl IccBond column (Analytichem Int product No. 617101). An aqueous fraction is eluted with 250 µl of 0.1M KOH. Squalene is then eluted with 1.0 ml 10% ethyl acetate in hexane and radioactivity determined. The difference in radioactivity in the presence and absence of the test compound is used to determine the level of inhibition. If the test compound inhibits at greater than about 70% at 25 micromolar, it is generally re-tested at 25 and 2.5 micromolar. The $IC_{50}$ (concentration which results in a 50% inhibition of squalene production), of the test compound can be determined by testing the compound at several, for example five, concentrations predicted from the two concentration results. The $IC_{50}$ can then be determined from a plot of percentage inhibition against concentration of test compound.

In general, compounds of formula I show significant inhibition in the above test at a concentration in the range of about 0.001 to 25 pM.

By way of illustration of the squalene synthase inhibitory properties of the compound of formula I, described in Example 5 below gave an $IC_{50}$ of $1.4 \times 10^{-7}$M.

(b) Acute rat cholesterol synthesis assay.

This is an acute in vivo test in the rat to measure de novo hepatic cholesterol synthesis from exogenously administered $^{14}$C-acetate.

Female rats (35 –55g) are housed in reverse lighting conditions (red light from 0200 h –1400h) for a period of about 2 weeks prior to test. Animals are allowed free access to chow and drinking water throughout this period. At test, animals should weigh 125–150 g.

Test compounds may be administered by oral gavage, dissolved or suspended in 0.5% polysorbate, or by ip or iv dosing. Control animals receive vehicle alone. After 1 hour the rats are injected ip with 25 µCi [2- 14C]-acetate (NEN DUPONT. specific activity, 45–60OmCi/mmol NEC-085H, or AMERSHAM specific activity, 50–60OmCi/mmol CFA 14) in a volume of 0.25 ml saline (100 µCi/ml). After a further hour, rats are terminally anaesthetised with halothane and a blood sample obtained from the abdominal vena cava.

1 ml of plasma is lyophilised and then saponified in 2ml ethanolic KOH (1 part 33% KOH, 9 parts ethanol) at 75° C. for 2 hours. After addition of an equal quantity of water, non-saponifiable lipids are extracted with two 5 ml volumes of hexane. The hexane extracts are evaporated to dryness and the residues dissolved in ethanol to determine cholesterol specific radioactivity. $EC_{50}$ values can be determined in the standard way.

In general, compounds of formula I show activity in the range of about 0.1 to 100 mg/kg. By way of illustration of the squalene synthase inhibitory properties of the compound of formula I, described in Example 17 below gave an $ED_{50}$ of 11 mg/kg.

No overt toxicity was detected when compounds of the formula I were administered at several multiples of their minimum inhibitory dose or concentration.

As mentioned above, the compounds of the present invention are squalene synthase inhibitors and hence possess the property of inhibiting cholesterol biosynthesis. Thus the compounds of the present invention will be useful in treating diseases or medical conditions in which an inhibition of squalene synthase is desirable, for example those in which a lowering of the level of cholesterol is blood plasma is desirable. In particular, the compounds of the present invention will be useful in treating hypercholesterolemia and/or ischaemic diseases associated with atheromatous vascular degeneration such as atherosclerosis. The compounds of the present invention will also be useful in treating fungal infections.

Thus according to a further feature of the present invention there is provided a method of inhibiting squalene synthase in a warm-blooded animals (such as man) requiring such treatment, which method comprises administering to said animal an effective amount of a compound of formula I (as herein defined), or a pharmaceutically-acceptable salt thereof. In particular, the present invention provides a method of inhibiting cholesterol biosynthesis, and more particularly to a method of treating hypercholesterolemia and atheromatous vascular degeneration (such as atherosclerosis).

Thus the present invention also provides the use of a compound of formula I (as herein defined), or a pharmaceutically-acceptable salt thereof, for the manufacture of a medicament for treating diseases or medical conditions in which a lowering of the level of cholesterol in blood plasma is desirable (such as hypercholesterolemia and atherosclerosis).

When used in the treatment of diseases and medical conditions in which an inhibition of cholesterol biosynthesis is desired, for example in the treatment of hypercholesterolemia or atherosclerosis, it is envisaged that a compound of formula I (or a pharmaceutically acceptable salt thereof) will be administered orally, intravenously, or by some other medically acceptable route so that a dose in the general range of, for example, 0.01 to 50 mg per kg body weight is received. However it will be understood that the precise dose administered will necessarily vary according to the nature and severity of the disease, the age and sex of the patient being treated and the route of administration.

In general, the compounds of formula I (or a pharmaceutically-acceptable salt thereof) will usually be administered in the form of a pharmaceutical composition, that is together with a pharmaceutically acceptable diluent or carrier, and such a composition is provided as a further feature of the present invention.

A pharmaceutical composition of the present invention may be in a variety of dosage forms. For example, it may be in the form of tablets, capsules, solutions or suspensions for oral administration, in the form of a suppository for rectal administration; in the form of a sterile solution or suspension for parenteral administration such as by intravenous or intramuscular injection.

A composition may be obtained by conventional procedures using pharmaceutically acceptable diluents and carriers well known in the art. Tablets and capsules for oral administration may conveniently be formed with a coating, such as an enteric coating (for example, one based on cellulose acetate phthalate), to minimise dissolution of the active ingredient of formula I (or a pharmaceutically-acceptable salt thereof) in the stomach or to mask unpleasant taste.

The compounds of the present invention may, if desired, be administered together with (or sequentially to) one or more other pharmacological agents known to be useful in the treatment of cardiovascular disease, for example, together with agents such as HMG-CoA reductase inhibitors such as lovastatin, bile acid sequestrants other hypocholesterolaemic agents such as fibrates, for example gemfibrozil and nicotinic acid, and drugs for the treatment of coronary heart disease. As a further example, the compounds of the present invention may, if desired, be administered together with (or sequentially to) an angiotensin converting enzyme (ACE) inhibitor, such as captopril, lisinopril, zofenopril or enalapril.

The compounds of the present invention may also find utility as antifungal agents, and so the present invention also provides a method of treating fungal infections which comprises administration to an a warm blooded animal, such as man, in need of such treatment an effective amount of a compound of formula I, or a pharmaceutically acceptable salt thereof. When used in this way the compounds of the present invention may, in addition to the formulations mentioned above, be adapted for topical administration and such a composition is provided as a further feature of the present invention. Such compositions may be in a variety of forms, for example creams or lotions.

The invention will now be illustrated by the following non-limiting Examples in which, unless otherwise stated:

(i) evaporations were carried out by rotary evaporation in vacuo;

(ii) operations were carried out at room temperature, that is in the range 18–26° C.;

(iii) yields are given for illustration only and are not necessarily the maximum attainable by diligent process development;

(iv) proton NMR spectra were normally determined at 200 MHz in deuterated water as solvent (unless stated otherwise), using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d,doublet;

(v) all end-products were characterised by microanalysis, NMR and/or mass spectroscopy;

(vi) conventional abbreviations are used for individual radicals and recrystallisation solvents, for example, Me=methyl, Et=ethyl, Pr=Propyl, $Pr^i$=isopropyl, Bu=butyl, $Bu^i$=isobutyl, Ph=phenyl; EtOAc=ethyl acetate, $Et_2O$=ether, MeCN=acetonitrile, MeOH= methanol, EtOH=ethanol, $Pr^iOH$=2-propanol, $H_2O$= water; and (vii) flash column chromatography or medium pressure liquid chromatography (MPLC) was performed on silica gel [either Fluka Kieselgel 60 (catalogue no. 60738) obtained from Fluka AG, Buchs, Swtizerland, or Merck Kiesselgel Art. 9385, obtained from E Merck, Darmstadt, Germany].

EXAMPLE 1

A solution of 4-bromobiphenyl (2.3 g) in tetrahydrofuran (5.0 ml) was added dropwise to a stirred suspension of magnesium turnings (240 mg) in tetrahydrofuran (5.0 ml). After the reaction had been initiated with a few drops of iodoethane, the reaction was heated at reflux until all the magnesium had been consumed (approximately one hour). The mixture was then cooled to ambient temperature, and a solution of 3-quinuclidinyl acetonitrile (750 mg) in tetrahydrofuran (5.0 ml) was then added to the stirred mixture. The reaction mixture was stirred for sixteen hours at ambient temperature and then stirred at reflux for one hour. The mixture was cooled, saturated ammonium chloride added and the mixture extracted with ether. The ether extract was separated, dried (MgSO$_4$) and evaporated. The residue was treated with 4M aqueous hydrochloric acid solution and the mixture was heated on a steam bath for 30 minutes. The mixture was then cooled, basified with 4H aqueous sodium hydroxide solution and extracted with ether. The ether extract was separated, dried (MgSO$_4$), filtered and an excess of ethereal hydrogen chloride was added to give a gum. The ether was decanted off and the gum was crystallised from ethanol to give 3-(biphenyl-4-ylcarbonylmethyl)quinuclidine hydrochloride as a solid (80 mg) m.p. 247° C.; microanalysis, found: C, 72.8; H, 7.2; N, 4.0%; C$_{21}$H$_{23}$NO.HCl 0.25H$_2$O requires C, 72.8; H, 7.08; N, 4.04%; NMR (D$_2$O): 1.9–2.25 (5H, m), 2.5–2.7(1H, m), 2.82–3.0(1H, m), 3.18–3.22(2H d), 3.28–3.6(4H, m), 3.65–3.8(1H, t), 7.55–7.8(7H, m), 7.9–8.0(2H, d); m/z 306(H+H).

The preparation of 3-quinuclidinyl acetonitrile is described, for example, in British Patent No. 1,416,958.

EXAMPLE 2

Potassium-tert-butoxide (1.12 g) was added to a stirred suspension of the 4-biphenylmethyl triphenyl phosphonium chloride (4.4 g) in dry tetrahydrofuran (60 ml) under argon. The deep orange-red reaction mixture was stirred for 30 minutes. The reaction mixture was then cooled to −40° C. and a solution of 3-formyl quinuclidine (570 mg) in dry tetrahydrofuran (5.0 ml) was added dropwise over 10 minutes. The reaction mixture was allowed to warm to ambient temperature and the reaction mixture stirred at this temperature for 16 hours. The tetrahydrofuran was evaporated and the residue dissolved in dichloromethane. The solution was washed with water, dried (MgSO$_4$) and evaporated to give semi-solid mass which was purified by flash column chromatography (Merck 9385 silica gel) using an eluent of 10% methanol in dichloromethane to remove triphenylphosphine oxide, followed by an eluant of 10% methanol in dichloromethane containing 1% 0.880 ammonia to give Z-3-[2-(biphenyl-4-yl)vinyl]quinuclidine (Rf=0.72). This was dissolved in ethanol and an excess of ethereal hydrogen chloride added followed by ether until crystallisation began. The solid was collected by filtration and dried to yield Z-3-[2-(biphenyl-4-yl)vinyl]quinuclidine hydrochloride as a colourless solid (90 mg), m.p. 216–217° C.; microanalysis, found C, 76.1; H, 7.4; N, 4.4%; C$_{21}$H$_{23}$N.HCl.0.25H$_2$O requires C, 76.3; H, 7.4; N, 4.2; NMR (D$_2$O) 1.8–2.15(5H, m), 2.15–2.4(1H, m), 3.02–3.6(6H, m), 5.89–6.0(1H, t), 6.3–6.76(1H, d, J=12 Hertz), 7.3–7.4(2H, d), 7.4–7.6(3H, m), 7.6–7.8(4H, t); m/z 290 (M+H).

Further elution with the above eluent gave (after fractions containing mixed isomers) pure E-3-[2-(biphenyl-4-yl)vinyl]-quinuclidine (Rf=0.6) which was converted to the hydrochloride salt as above to give E-3-[2-(biphenyl-4-yl)vinyl]quinuclidine hydrochloride (65 mg), m.p. >300° C., microanalysis, found C, 73.4; H, 7.6; N, 4.3%; C$_{21}$H$_{23}$N.HCl.H$_2$O requires C, 73.36, H, 7.57, N, 4.07%; NMR (D$_2$O): 1.8–2.2(5H, m), 2.8–3.0(1H, m), 3.1–3.22(1H, m), 3.3–3.7(5H, m), 6.25–6.4(1H, dd), 6.5–6.6(1H, d, J=14.4 Hertz), 7.43–7.6(5H, m), 7.6–7.78(4H, m); m/z 290 (M+H).

The 4-biphenylmethyltriphenyl phosphonium chloride was prepared by stirring a mixture of triphenyl phosphine (7.86 g) and 4-chloromethyl biphenyl (2.02 g) at 160° C. for one hour (a thick solid was formed). The reaction mixture was cooled, ethanol (20 mls) was added and the mixture heated under reflux until complete dissolution was obtained. Hexane (80 ml) was then added slowly to the solution, and the mixture then cooled, to give a thick white precipitate. This solid was collected by filtration and washed with ether to give 4-biphenylmethyl triphenyl phosphonium chloride (4.6 g), m.p. 283–284° C.

EXAMPLE 3

10% palladium on carbon (40 mg) was added to a stirred solution of ammonium formate (250 mg) and a mixture of E/Z isomers of 3-[2-(biphenyl-4-yl)vinyl]quinuclidine (243 mg) in methanol (10 ml). The mixture was heated at 60° C. with stirring for one hour. A further quantity of ammonium formate (500 mg) was then added, and the reaction mixture heated at 60° C. for a further hour. The reaction mixture was cooled, filtered through diatomaceous earth and the residues washed with methanol. The methanol filtrates were combined and evaporated. The residue was partitioned between 4M aqueous sodium hydroxide solution and dichloromethane. The organic layer was separated, dried (MgSO$_4$) and evaporated to give a colourless oil. This oil was purified by flash column chromatography on silica (Merck 9385), using an eluent of 10% methanol in dichloromethane containing 1% 0.880 ammonia. The purified product was then dissolved in acetone, and an excess of ethereal hydrogen chloride was then added, followed by sufficient ether to cause crystallisation. The solid was collected by filtration to give 3-[2-(biphenyl-4-yl)ethyl]quinuclidine hydrochloride as a colourless solid (115 mg), m.p. 223–224° C.; microanalysis, found C,76.5; H, 8.1; N, 4.5%; C$_{21}$H$_{25}$N.HCl, requires C,76.9; H, 7.99; N, 4.27%; NMR (D$_2$O), 1.6–2.1(8H, m), 2.5–2.65(2H, t), 2.75–2.9(1H, m), 3.1–3.5(5H, m), 7.22–7.32(2H, d), 7.32–7.52(3H, m), 7.55–7.65(2H, d), 7.65–7.75(2H, d); m/z 292(M+H).

EXAMPLE 4

4-Biphenylcarboxaldehyde (160 mg) and 3-aminoquinuclidine (110 mg) were heated under reflux in toluene (50 ml) for 2 hours using a Dean and Stark water separator. The toluene was evaporated and the residue was purified by medium pressure column chromatography on alumina (ICN Alumina N 32–63), eluting with ethyl acetate to give 3-[(biphenyl-4-ylmethylene)amino]quinuclidine (150 mg) as a colourless solid, m.p. 82–84° C.; microanalysis, found: C, 82.2; H, 7.7; N, 9.6%; C$_{20}$H$_{22}$N$_2$ requires: C, 82.7; H, 7.6; N, 9.6%; NMR (CDCl$_3$): 1.35–1.5 (1H, m), 1.6–1.8(3H, m), 2.2–2.3(1H, m), 2.8–3.0(4H, m), 3.0–3.2(2H, m), 3.4–3.5(1H, m), 7.3–7.5(3H, m), 7.55–7.65 (4H, m), 7.8(2H, dd) and 8.3(1H, s); m/z 291 (M+H).

EXAMPLE 5

Sodium borohydride (260 mg) was added to a stirred solution of 3-[(biphenyl-4-ylmethylene)amino]quinuclidine (990 mg) in methanol (50 ml) and the reaction mixture stirred for 2 hours. The methanol was evaporated and the residue dissolved in IM hydrochloric acid (12 ml). The aqueous solution was washed with diethyl ether (3×25 ml) before the addition of excess sodium hydroxide solution (density 1.35 g/cm$^3$) to pH 14. The mixture was extracted with diethyl ether, the ether separated, dried (Na$_2$SO$_4$) and evaporated. An excess of saturated ethereal hydrogen chloride was added to precipitate a solid which was crystallised from methanol/ethyl acetate to give 3-1[(biphenyl-4-ylmethyl)amino]quinuclidine (820 mg) as a colourless solid, m.p. 180–181° C., microanalysis, found: C, 62.8; H, 7.3; N, 7.4%; C$_{20}$H$_{24}$N$_2$2HCl.H$_2$O requires: C, 62.7; H, 7.3; N, 7.3%; NMR: ([CD$_3$]$_2$SO): 1.7–2.0(3H, m), 2.2–2.4(1H, m), 2.6(1H, s), 3.1–3.8(8H, m), 4.2(2H, s), 7.3–7.5(3H, m) and 7.6–7.8(6H, m); m/z 293 (H+H).

EXAMPLE 6

A solution of sodium hydroxide (9.1 g) in water (91 ml) was added at ambient temperature to a stirred mixture of quinuclidin-3-one (9.5 g), 4-phenylphenol (13.7 g), trimethylsulphoxonium iodide (33.4 g), and tetrabutyl-ammonium hydrogen sulphate (1.2 g), in toluene (150 ml). The mixture was stirred at ambient temperature for 2 days under argon. Saturated brine (220 ml) was added to the mixture and the mixture was extracted with ethyl acetate (4×140 ml). The ethyl acetate extracts were combined, dried ($Na_2So_4$) and evaporated to give a residue which was purified by flash column chromatography on silica (Merck 9358, 264 g). This material was further purified by recrystallisation from ethyl acetate to give 3-(biphenyl-4-yloxymethyl)quinucldin-3-ol (0.8 g) as a colourless solid, m.p. 132–133° C.; microanalysis, found: C, 76.5; H, 7.4; N, 4.8%; $C_{20}H_{23}NO_2$ $0.2H_2O$ requires: C, 76.7; H, 7.5; N, 4.5%; NMR ($CDCl_3$): 1.3–1.5(1H, m), 1.5–1.7(2H, m), 2.0–2.2(2H, m), 2.3–2.7 (1H, br), 2.6–3.1(6H, m), 3.9(1H, d), 4.1(1H, d), 7.0(2H, d), 7.2–7.6(7H, m); m/z 310 (M+H).

EXAMPLE 7

A solution of sodium hydroxide (9.1 g) in water (90 ml) was added at ambient temperature to a stirred mixture of quinuclidin-3-one (9.5 g), 4-phenylthiophenol (13.2 g), and trimethylsulphoxonium iodide (33.4 g) in toluene (150 ml). The reaction mixture was stirred at ambient temperature for 3 days under an atmosphere of argon. The reaction mixture was filtered through diatomaceous earth. The majority of the required product was held in the filtercake. The filtercake was washed with ethyl acetate and then extracted with methanol (4×130 ml). The methanol extracts were combined and evaporated to give a residue which was suspended in 1H aqueous sodium hydroxide solution (250 ml) and extracted with ethyl acetate (2×260 ml and 2×130 ml). The ethyl acetate extracts were combined, washed with saturated brine (50 ml), and extracted with 2H aqueous hydrochloric acid solution (8×25 ml). The hydrochloride salt crystallised from the combined aqueous solution to give 3-(biphenyl-4-ylsulphanylmethyl)quinuclidin-3-ol hydrochloride (11.9 g) as a colourless solid, m.p. 107–109° C.; microanalysis, found: C, 63.4; H, 7.0; N, 3.7%; $C_{20}H_{23}NOS \cdot HCl \cdot H_2O$ requires: C, 63.2; H, 6.9; N, 3.7%; m/z 326 (M+H).

The aqueous filtrate was cooled in ice, basified with 32% w/w aqueous sodium hydroxide solution (50 ml) and extracted with ethyl acetate (3×130 ml). The ethyl acetate extracts were combined, dried ($Na_2So_4$) and evaporated to give 3-(biphenyl-4-ylsulphanylmethyl)-quinuclidin-3-ol (0.5 g) as a colourless solid, m.p. 145–147° C.; microanalysis, found: C, 73.6; H, 7.2; N, 4.3%; $C_{20}H_{23}NOS$ requires: C, 73.8; H, 7.1; N, 4.3%; NMR ($CDCl_3$): 1.2–1.4 (1H, m), 1.5–1:6(2H, m), 1.9–2.0(1H, quin), 2.0–2.2(1H, m), 2.5–3.0(7H, m), 3.1–3.5(2H, q) and 7.2–7.6(9H, m); m/z 326 (M+H).

EXAMPLE 8

Sodium metaperiodate (2.5 g) was added to a solution of 3-(biphenyl-4-ylsulphanylmethyl)quinuclidin-3-ol hydrochloride (1.1 g) in methanol (10 ml). The mixture was stirred at ambient temperature for 5 hours and the solvent was then removed by evaporation. Water (15 ml) was added to the residue, the ice-cooled mixture was treated with 32% w/w aqueous sodium hydroxide solution and extracted with ethyl acetate (3×50 ml.) The ethyl acetate extracts were combined, dried ($Na_2So_4$) and evaporated. The residue was purified by flash column chromatography on silica gel using a 95:5:3 v/v mixture of ethyl acetate, methanol and 35% w/w ammonia solution as eluent to give a 2:1 mixture of diastereomers of 3-(biphenyl-4-ylsulphinylmethyl)quinuclidin-3-ol (0.3 g) as a colourless solid, m.p. 157–162° C.; microanalysis, found: C, 68.9; H, 6.8; N, 3.9%; $C20H_{23}NO_2S$ requires: C, 69.1; H, 6.9; N, 4.0%; NMR ($CDCl_3$): 1.3–1.9(3H, m), 2.0(<1H, m minor diastereomer), 2.1–2.4(1H, m), 2.5(<1H, m major diastereomer), 2.6–3.1(7H, m), 3.0–3.2(2H, q), 3.1–3.2(1H, m), 4.1–4.6(1H, br), 7.35–7.55(3H, m), 7.55–7.65(2H, m) and 7.65–7.8(4H, m) m/z 342 (M+H).

EXAMPLE 9

Potassium peroxymonosulphate as "oxone" (Trademark) (1.85 g) was added to a solution of 3-(biphenyl-4-ylsulphanylmethyl)quinuclidin-3-ol hydrochloride (1.1 g) in methanol (20 ml). The mixture was stirred at ambient temperature for 4 hours. The mixture was filtered and the filtercake was washed with methanol. The methanol filtrate and washings were combined and evaporated. The residue was treated with ice-cooled 16% w/w sodium hydroxide solution (35 ml) and extracted with ethyl acetate (3×50 ml). The ethyl acetate extracts were combined, concentrated to 60 ml by evaporation and allowed to crystallise. The solid was recrystallised twice from methanol to give 3-(biphenyl-4-ylsulphonylmethyl)quinuclidin-3-ol (0.3 g) es a colourless solid, m.p. 203–205° C.; microanalysis, found: C, 66.3; H, 6.5; N, 3.8%; $C_{20}H_{23}NO_3S$ requires: C, 66.4; H, 6.5; N, 3.9%; NMR (DMSO-$d_6$): 1.1–1.2(1H, m), 1.3–1.7(2H, m), 1.8–2.0(2H, m), 2.5–2.8(5H, m), 3.0(1H, d), 3.5–3.8(2H, q), 4.7(1H, s), 7.4–7.6(3H, s), 7.6–7.8(2H, m) and 7.8–8.0(4H, m); m/z 358 (M+H).

EXAMPLE 10

A solution of n-butyl lithium in n–hexane (6.4 ml, 1.6H) was added dropwise to a stirred solution of 1-biphenyl-2,2-dibromoethylene (1.2 g) in dry tetrahydrofuran (15 ml) at −60° C. under an atmosphere of argon. The cooling bath was removed and the reaction mixture was stirred at ambient temperature for 1 hour. The reaction mixture was then cooled to −60° C. and a solution of quinuclidin-3-one in dry tetrahydrofuran (5.0 ml) was added dropwise over a period of 10 minutes. The reaction mixture was stirred for a further 1 hour and then quenched by the slow addition of water (1.0 ml). The tetrahydrofuran was removed by evaporation to give a residue which was crystallised from methanol to give 3-[2-(biphenyl-4-yl)ethynyl]quinuclidin-3-ol as a colourless solid (300 mg), m.p. 217–218° C.; microanalysis, found C, 83.2; H, 7.0; N, 4.8%; $C_{21}H_{21}NO$ requires C, 83.1; H, 6.98; N, 4.62%; NMR (DMSO-$d_6$): 1.2–1.4(1H, m), 1.5–1.7(1H, m), 1.8–2.02(3H, m), 2.6–2.78(4H, t), 2.8–2.92(1H, d), 3.02–3.14(1H, d), 5.61(1H, s), 7.32–7.54(5H, m), 7.62–7.73 (4H, m); m/z 304 (N+H).

The 1-biphenyl-2,2-dibromoethylene used as starting material was prepared as follows.

Carbon tetrabromide (25.2 g) was added to a stirred solution of triphenylphosphine (26. 2 g) in dry dichloromethane (600 ml). The reaction mixture was stirred for 15 minutes and Zinc dust (6.5 g) was then added in one portion and the reaction mixture stirred overnight at ambient temperature. Biphenyl-4-carboxyaldehyde (9.1 g) was then added to the reaction mixture and the reaction mixture stirred for 3 hours. A further quantity of triphenyl phosphine (5.2 g) and carbon tetrabromide (5.0 g) was then added to the reaction mixture. The reaction mixture was stirred for a further 3 hours at ambient temperature and the dichloromethane was then removed by evaporation. The residue was extracted with boiling hexane (4×200 ml) and filtered whilst hot. The filtrates were combined and concentrated to 400 ml by evaporation when colourless crystals formed of 1-biphenyl-2,2-dibromoethylene (9.6 g), m.p. 105–106° C.; NMR (CDCl$_3$) 7.3–7.7 (10H, m); m/z 336+338+340 (M+H)

EXAMPLE 11

A mixture of 3-[2-(biphenyl-4-yl)ethynyl]quinuclidin-3-ol (303 mg), ammonium formate (800 mg) and 5% palladium on carbon (50 mg) in methanol (20 ml) was stirred at 60°C. for 30 minutes. Further 100 mg portions of ammonium formate were then added at 20 minutes intervals over 1 hour whilst maintaining the reaction temperature at 60° C. The reaction mixture was then cooled and filtered through diatomaceous earth and washed with methanol. The filtrate and methanol washings were combined and evaporated. The residue was dissolved in water, basified by addition of 4M aqueous sodium hydroxide solution and extracted with dichloromethane (3×10 ml). The organic extracts were combined, dried (Na$_2$So$_4$) and an excess of ethereal hydrogen chloride added. Ether (30ml) was then added to yield a precipitate which was collected by filtration and washed with with ether to give 3-[2-(biphenyl-4-yl)ethyl]-quinuclidin -3-ol hydrochloride (280 mg) as a solid, m.p. 224–225° C.; microanalysis, found: C, 72.2; H, 7.6; N, 4.1%; C$_{21}$H$_{25}$NO.HCl. 0.3H$_2$0 requires C, 72.2; H, 7.6; N, 4.0%; NMR (DMSO-d$_6$): 1.58–2.1(5H, m), 2.15–2.32(1H, m), 2.56–2.86(2H, m), 2.92–3.3(7H, m), 5.16(1H, s), 7.28–7.7(9H, m); m/z 308 (M+H).

EXAMPLE 12

A mixture of 3-[2-(biphenyl-4-yl)ethynyl]quinuclidin-3-ol (303 mg) and p-toluenesulphonic acid (570 mg) was stirred at reflux in toluene (25 ml) for 4 hours. The reaction mixture was cooled and the toluene removed by evaporation. The residue was treated with saturated sodium carbonate solution (10 ml) and extracted with ethyl acetate (2×10 ml). The organic extract was dried (MgSO$_4$) and evaporated to give a gum (300 mg). This gum was successively crystallised from a 1:1 v/v mixture of ethyl acetate and n-hexane, and then n-hexane to yield 2,3-dehydro-3-(biphenyl-4-ylmethylcarbonyl)quinuclidine (22 mg)as a solid, m.p. 147.3° C.; microanalysis, found: C, 83.2; H, 6.9; N, 4.6%; C$_{21}$H$_{21}$NO requires C, 83.1; H, 6.98; N, 4.62%; NMR (DMSO-d$_6$): 1.47–1.73(4H, m), 2.6–2.95(5H, m), 3.9(2H, s), 7.08–7.12(1H, t), 7.37–7.57(3H, m), 7.7–7.88(4H, m) and 8.02–8.12(2H, d); m/z 304 (M+H).

EXAMPLE 13

Sodium hydride (60% w/w dispersion in mineral oil; 80 mg) was added portionwise over a period of 10 minutes to a stirred solution of 4(cyanomethyl)biphenyl (386 mg) in xylene (10 ml) under an atmosphere of argon. The reaction mixture was then stirred at ambient temperature for a further 30 minutes. Quinuclidine-3-carboxylic acid methyl ester (340 mg) was then added and the reaction mixture was stirred at reflux under an atmosphere of argon for 6 hours. The reaction mixture was cooled and ether (20 ml) was added. The solid obtained was collected by filtration and added to concentrated hydrochloric acid (15 ml). The resulting mixture was stirred at reflux for 6 hours. The reaction mixture was cooled and evaporated to small volume and basified by the addition of saturated sodium carbonate solution. The resulting mixture was extracted with ethyl acetate (3×15 ml). The ethyl acetate extracts were combined, dried (MgSO$_4$) and evaporated to give a gum (290 mg). This gum was purified by flash column chromatography on alumina (ICN Alumina N 32–63) using 10% methanol in ethyl acetate as eluent to give 3-[2-(biphenyl-4-yl) methylcarbonyl]quinuclidine (150 mg) as a gum. The gum was dissolved in ethyl acetate and an excess of ethereal hydrogen chloride added. The precipitated gum was separated from the liquor and crystallised from a mixture of 2-propanol and ether to give 3-[2-(biphenyl-4-yl) methylcarbonyl]quinuclidine hydrochloride (100 mg) as a solid, m.p. 189° C.; microanalysis, found: C, 73.7; H, 7.1; N, 4.0%; C$_{21}$H$_{23}$NO.HCL requires C, 73.8, H, 7.08, N, 4.1%; NMR (DMSO-d$_6$): 1.48–1.68(1H, m), 1.68–1.88(1H, m), 1.93–2.12(2H, m), 2.65–2.75(1H, q), 3.05–3.47(6H, m), 3.58–3.7(1H, d of d), 3.9–4.1(2H, d of d), 7.28–7.52(5H, m), 7.6–7.7(4H, m); m/z 305 (H+H).

The 4-(cyanomethyl)biphenyl used as starting material was prepared as follows.

Potassium cyanide (2.6g) was added to a stirred, two-phase mixture of 4-(chloromethyl)biphenyl (2.02g) and tetrabutyl ammonium hydrogen sulphate (200 mg) in dichloromethane (50 ml). The reaction mixture was stirred at ambient temperature for 36 hours. The organic layer was separated and washed with water (10 ml), dried (MgSO$_4$) and evaporated to give a solid residue which was crystallised from n-hexane to give 4-(cyanomethyl)biphenyl (1.3g) as a solid, m.p. 95° C.; microanalysis, found: C, 86.3; H, 5.7; N, 7.2%; C$_{14}$H$_{11}$N .O.1H$_2$O requires C, 86.2; H, 5.7; N, 7.18%.

Quinuclidine-3-carboxylic acid methyl ester is readily available (see for example, Helvetica Chimica, (1954), 37, 1689–1698).

EXAMPLE 14

A stirred mixture of 4-bromo-4'-ethoxybiphenyl (1.1 g), 3-ethynyl-3-hydroxyquinuclidine (600 mg), bis (triphenylphosphine)-palladium (II) chloride (140 mg), copper (I) iodide (70 mg) and dry triethylamine (5.0 ml) in dry dimethylformamide (20 ml) was stirred at 90° C. under an atmosphere of argon for 4 hours. The dimethylformamide and triethylamine were removed by evaporation and the residue was treated with saturated sodium carbomate solution (20 ml). The solid obtained was collected by filtration and crystallised from dimethylformamide to give 3-[2-(4'-ethoxybiphenyl-4-yl)ethynyl]quinuclidin-3-ol (300 mg) as a soild, m.p. 255–256° C.; microanalysis, found C, 79.1; H, 7.3; N, 3.9%; C$_{23}$H$_{25}$ NO2 requires C, 79.5; H, 7.3; N, 4.03%; NMR (DMSO-d$_6$): 1.2–.1.4(3H, t), 1.52–1.71(1H, m), 1.8–2.0(3H, m), 2.6–2.98(5H, m), 3.05–3.2(1H, m), 4.0–4.16(2H, q), 5.51–5.62(1H, br), 6.95–7.05(2H, d), 7.4–7.5(2H, d) an 7.57–7.68(4H, m); m/z 348 (M+H).

The 3-ethynyl-3-hydroxyquinuclidine used as starting material was obtained as follows:

A solution of n-butyl lithium (100 ml of a 2M solution in pentane) was added portion-wise over a period of 20 minutes to a stirred solution of ethynyltrimethylsilane (19.6 g) in dry tetrahydrofuran (400 ml) at −70° C. The mixture was stirred for 1 hour at −70° C. A solution of quinuclidin-3-one (2.4 g) in dry tetrahydrofuran (100 ml) was then added to the mixture and the mixture stirred for 1 hour at −70° C. Methanol (1 ml) was then added to the mixture and the mixture allowed to warm to room temperature. The solvents were removed by evaporation. Methanol (500 ml) and potassium carbonate (40 g) were added to the residue and the mixture was stirred for 1 hour. The solvent was removed by evaporation. The residue was triturated under water (500 ml) and the solid obtained dried in vacuo. There was thus obtained 3-ethynyl-3-hydroxy-quinuclidine as a solid, m.p. 193–197° C.; NMR (DMSO-d$_6$): 1.5–1.3(lH, m), 1.1–1.6 (1H, m), 1.7–1.95(3H, m), 2.55–2.8(5m), 2.95(IH, d), 3.3 (1H, d) and 5.4(1H, s); m/Z 152 (M+H).

EXAMPLE 15

A mixture of 4-bromo-4'-hydroxybiphenyl (747 mg), 3-ethynyl-3-hydroxyquinuclidine (453 mg), bis(triphenylphosphine)-palladium (II) chloride (105 mg), copper (I) iodide (55 mg) and dry triethylamine (5.0 ml) in dry dimethylformamide (10 ml) was stirred at 70° C. under an atmosphere of argon for 4 hours. The reaction mixture was cooled and the dimethylformamide and triethylamine were removed by evaporation. The residue was purified by flash column chromatography on alumina (ICN - Alumina N32-63) using a gradient of 10% methanol in ethyl acetate to 20% methanol in ethyl acetate as eluent to give 3-[(4'-hydroxybiphenyl-4-yl)ethynyl]quinuclidin-3-ol (220 mg) as a solid, m.p. 230–233° C.; microanalysis, found C, 76.7; H, 6.6, N, 4.4%; $C_{21}H_{21}NO_2 \cdot 0.5H_2O$ requires C, 76.8; H, 6.7; N, 4.26%; NMR (DMSO-$d_6$): 1.2–1.42(1H, m), 1.5–1.72 (1H, m), 1.8–2.0(3H, m), 2.65–2.8(4H, t), 2.8–3.2(2H, d of d), 5.6–5.7(1H, br), 6.8–6.9(2H, d) and 7.48–7.63(6H, m); m/z 320 (M+H).

EXAMPLE 16

A mixture of 4-bromo-4'-fluorobiphenyl (1.0 g), 3-ethynyl-3-hydroxyquinuclidine (600 mg), bis(triphenylphosphine)-palladium (II) chloride (120 mg) and copper (I) iodide (60 mg) in dry triethylamine (15 ml) was stirred at reflux under an atmosphere of argon for 5 hours. The reaction mixture was cooled, diluted with water (60 ml), 2H aqueous sodium hydroxide solution added and extracted with dichloromethane. The mixed layers were filtered through diatomaceous earth and washed with dichloromethane. The organic layer in the filtrate was separated, dried ($MgSO_4$) and evaporated to a residue which was further purified by flash column chromatography on alumina (ICN Alumina N 32–63) using a mixture of 10% ethanol in ethyl acetate as eluent to give a residue which was crystallised from a mixture of 10% ethanol in ethyl acetate to give 3-[2-(4'-fluorobiphenyl-4-yl)ethynyl]quinuclidin-3-ol (210 mg) as a solid, m.p. 232–233° C.; microanalysis, found: C, 78.0; H, 6.4; N, 4.5%; $C_{21}H_{20}FNO \cdot 0.1H_2O$ requires C,78.07; H,6.26; N, 4.34%; NMR (DMSO-$d_6$): 1.2–1.4(1H, m), 1.5–1.7(1H, m), 1.8–2.01(3H, m), 2.6–2.8(4H, t), 2.8–3.15(2H, d of d), 5.6(1H, s), 7.22–7.4(2H, m), 7.45–7.55(2H, d) and 7.61–7.81(4H, m); m/z 322 (M+H).

EXAMPLE 17

Using a similar procedure to that described in Example 6, but using 4,4'-dihydroxybiphenyl in place of 4-phenylphenol, there was thus obtained, after recrystallisation from methanol, 3-(4'-hydroxybiphenyl-4-yloxymethyl)quinuclidin-3-ol, m.p. 212–214° C.; microanalysis, found: C, 73.2; H, 7.2; N, 4.1%; $C_{20}H_{23}NO_3$ requires: C, 73.2; H, 7.2; N, 4.3%; NMR (DMSO-$d_6$): 1.13–1.32(1H, m), 1.32–1.67(2H, m), 1.85–2.10(2H, m), 2.45–2.9(6H, m), 3.82–4.13(2H, q), 4.64(1H, s), 6.8(2H, d), 7.0(2H, d), 7.35–7.55(4H, m) and 9.43(1H, br.s); m/Z 326 (M+H).

EXAMPLE 18

Illustrative pharmaceutical dosage forms suitable for presenting the compounds of the invention for therapeutic or prophylactic use include the following tablet and capsule formulations, which may be obtained by conventional procedures well known in the art of pharmacy and are suitable for therapeutic or prophylactic use in humans:

| (a) Tablet I | mg/tablet |
|---|---|
| Compound Z* | 1.0 |
| Lactose Ph. Eur. | 93.25 |
| Croscarmellose sodium | 4.0 |
| Maize starch paste (5% w/v aqueous paste) | 0.75 |
| Magnesium stearate | 1.0 |

| (b) Tablet II | mg/tablet |
|---|---|
| Compound Z* | 50 |
| Lactose Ph. Eur | 223.75 |
| Croscarmellose sodium | 6.0 |
| Maize starch | 15.0 |
| Polyvinylpyrrolidone (5% w/v aqueous paste) | 2.25 |
| Magnesium stearate | 3.0 |

| (c) Tablet III | mg/tablet |
|---|---|
| Compound Z* | 100 |
| Lactose Ph. Eur. | 182.75 |
| Croscarmellose sodium | 12.0 |
| Maize starch paste (5% w/v aqueous paste) | 2.25 |
| Magnesium stearate | 3.0 |

| (d) Capsule | mg/capsule |
|---|---|
| Compound Z* | 10 |
| Lactose Ph. Eur. | 488.5 |
| Magnesium stearate | 1.5 |

Note
*The active ingredient Compound Z is a compound of formula I, or a salt thereof, for example a compound of formula I described in any of the preceding Examples.

The tablet compostions (a)–(c) may be enteric coated by conventional means, for example, with cellulose acetate phthalate.

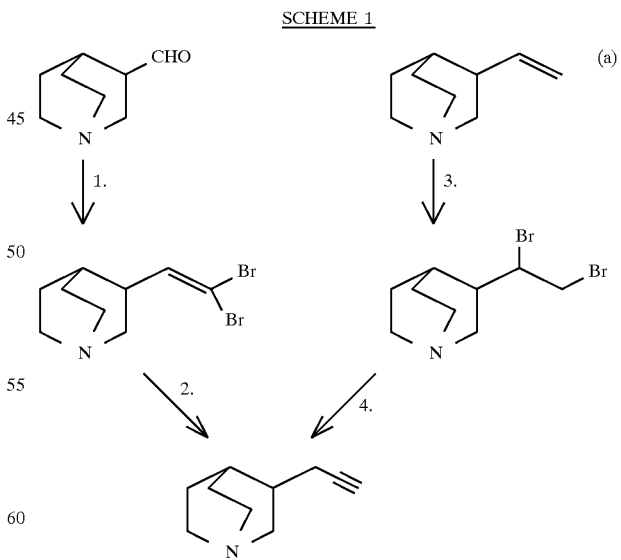

SCHEME 1

1. $CBr_4/PPh_3/Zn$, $CH_2Cl_2$, room temperature
2. (a) nBuLi (2 equiv), THF, −60° C., organ atmosphere (b) $H_2O$
3. $Br_2/H_2O$
4. t-BuOK, t-BuOH, reflux

SCHEME 1
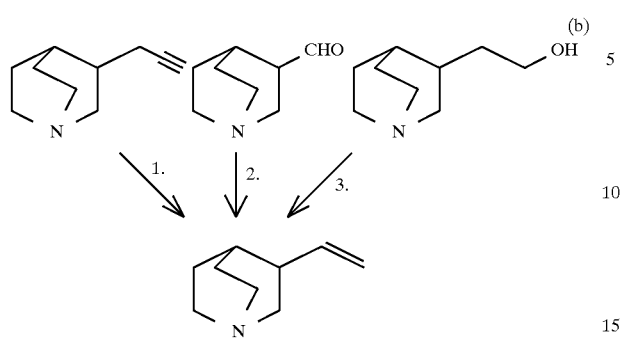
1. H₂/Pd—CaCO₃, EtOH
2. Ph₃PCH₃Br⊖, KOBuᵗ, THF
3. Phthalic anhydride, benzene sulphonic acid, 280° C.
SCHEMES 2
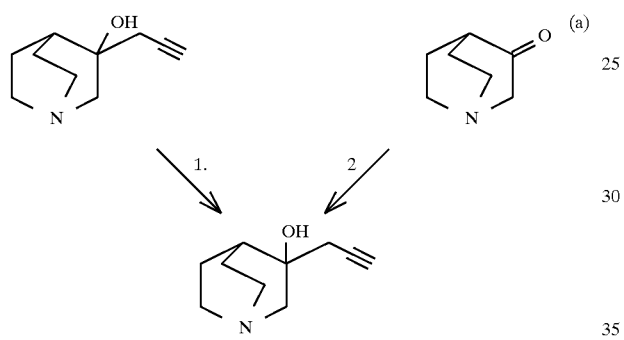
1. H₂/Pd—CaCO₃, EtOH
2. (a) ⟶ MgBr, THF, 20–25° C. (b) NH₄Cl solution
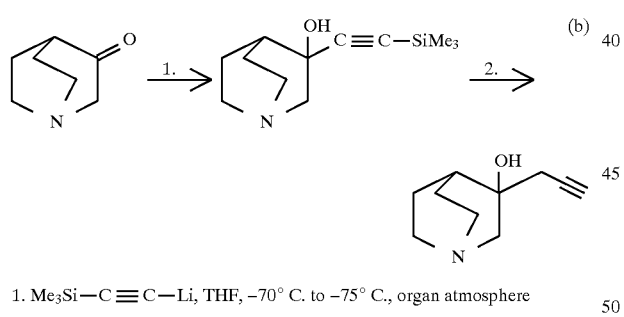
1. Me₃Si—C≡C—Li, THF, −70° C. to −75° C., organ atmosphere
2. K₂CO₃, MeOH, 20–25° C.
CHEMICAL FORMULAE
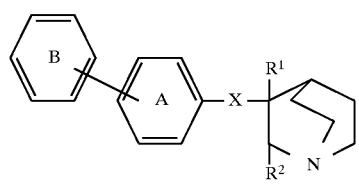  I
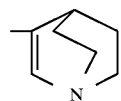  Ia
-continued
CHEMICAL FORMULAE
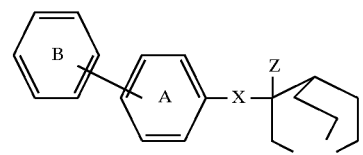  II
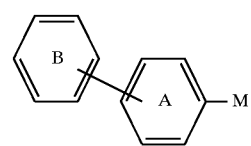  III
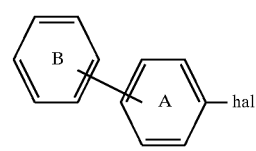  IIIa
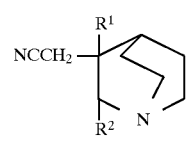  IV
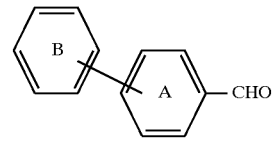  V
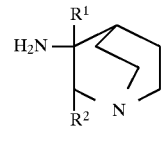  VI
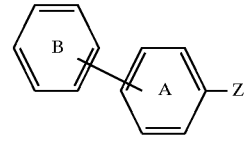  VII
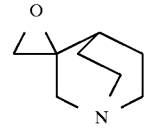  VIII
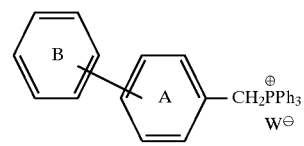  IX
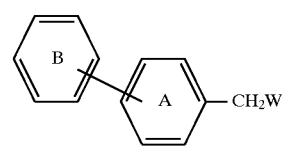  IXa
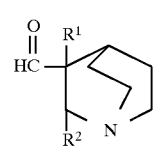  X -continued
CHEMICAL FORMULAE

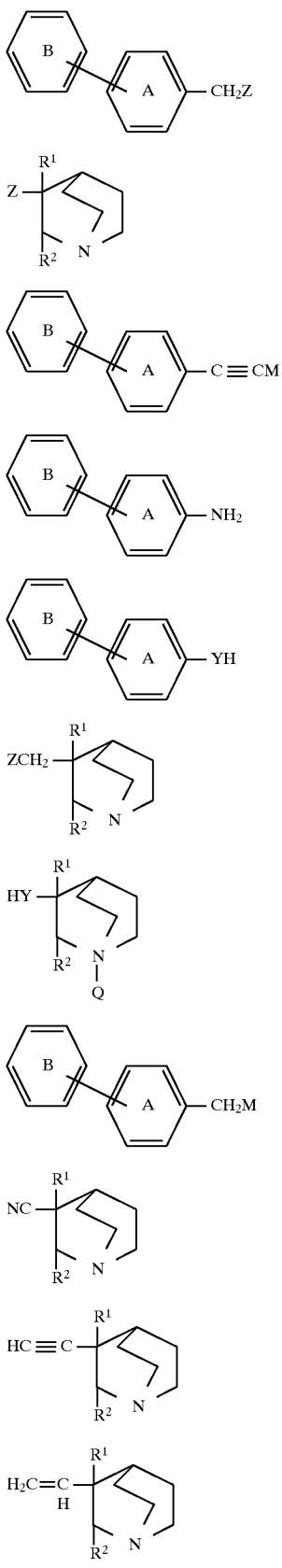

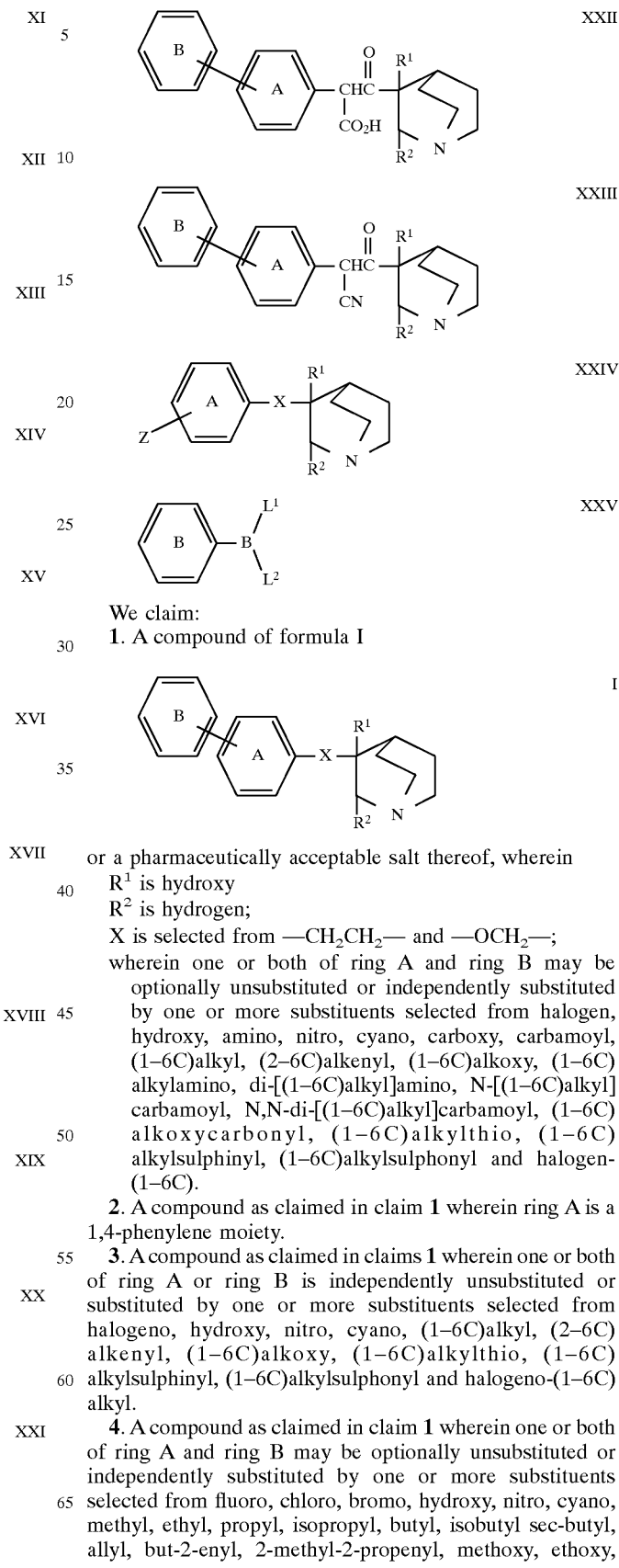

We claim:
1. A compound of formula I or a pharmaceutically acceptable salt thereof, wherein
$R^1$ is hydroxy
$R^2$ is hydrogen;
X is selected from —CH$_2$CH$_2$— and —OCH$_2$—;
wherein one or both of ring A and ring B may be optionally unsubstituted or independently substituted by one or more substituents selected from halogen, hydroxy, amino, nitro, cyano, carboxy, carbamoyl, (1–6C)alkyl, (2–6C)alkenyl, (1–6C)alkoxy, (1–6C)alkylamino, di-[(1–6C)alkyl]amino, N-[(1–6C)alkyl]carbamoyl, N,N-di-[(1–6C)alkyl]carbamoyl, (1–6C)alkoxycarbonyl, (1–6C)alkylthio, (1–6C)alkylsulphinyl, (1–6C)alkylsulphonyl and halogen-(1–6C).

2. A compound as claimed in claim 1 wherein ring A is a 1,4-phenylene moiety.

3. A compound as claimed in claims 1 wherein one or both of ring A or ring B is independently unsubstituted or substituted by one or more substituents selected from halogeno, hydroxy, nitro, cyano, (1–6C)alkyl, (2–6C)alkenyl, (1–6C)alkoxy, (1–6C)alkylthio, (1–6C)alkylsulphinyl, (1–6C)alkylsulphonyl and halogeno-(1–6C)alkyl.

4. A compound as claimed in claim 1 wherein one or both of ring A and ring B may be optionally unsubstituted or independently substituted by one or more substituents selected from fluoro, chloro, bromo, hydroxy, nitro, cyano, methyl, ethyl, propyl, isopropyl, butyl, isobutyl sec-butyl, allyl, but-2-enyl, 2-methyl-2-propenyl, methoxy, ethoxy, propoxy, isopropoxy, butoxy, methylthio, ethylthio, propylthio, isopropylthio, butylthio, methylsulphinyl, ethylsulphinyl, propylsulphinyl, isopropylsulphinyl, butylsulphinyl, methylsulphonyl, ethylsulphonyl, propylsulphonyl, isopropylsulphonyl, butylsulphonyl and trifluoromethyl.

5. A compound as claimed in claim 1 selected from:

3-(biphenyl-4-yloxymethyl)quinucldin-3-ol;and and their pharmaceutically acceptable salts.

6. A pharmaceutical composition which comprises a compound of formula I as claimed in claim 1, or a pharmaceutically acceptable salt thereof, together with a pharmaceutically acceptable diluent or carrier.

7. A method of inhibiting squalene synthase in a warm blooded animal requiring such treatment, which method comprises administering a squalene synthase inhibiting amount of a compound of formula I, or a pharmaceutically acceptable salt thereof, as defined in claim 1 to said animal.

8. A process for preparing a compound as claimed in claim 1, which process is selected from:

(g) for those compounds of formula I in which X is —OCH$_2$—, R$^1$ is hydroxy and R$^2$ is hydrogen, reacting a compound of formula VII in which Z is —OH, with a compound of formula VIII; and

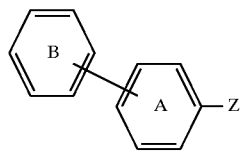

VII

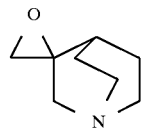

VIII (i) for those compounds of formula I in which X is —CH$_2$CH$_2$—, reducing a compound of formula I in which X is —CH=CH—;

and whereafter, when a pharmaceutically-acceptable salt of a compound of the formula I is required, reacting said compound with an acid which affords a physiologically acceptable anion, or with a base which affords a physiologically acceptable cation.

9. A method of treating a medical condition selected from hypercholesterolemia and atherosclerosis comprising administering to a warm-blooded animal in need thereof an effective amount of a compound of formula I, or a pharmaceutically acceptable salt thereof, as defined in claim 1.

* * * * *

UNITED STATES PATENT AND TRADEMARK OFFICE
CERTIFICATE OF CORRECTION

PATENT NO. : 5,770,608
DATED : June 23, 1998
INVENTOR(S) : Brown et al.

Page 1 of 1

It is certified that error appears in the above-identified patent and that said Letters Patent is hereby corrected as shown below:

Column 1,
First paragraph, change "This is a continuation of application Ser. No. 08/256,123 filed Jun. 23, 1994 now U.S. Pat. No. 5,654,315." to -- This is a continuation of application Ser. No. 08/256,123 filed Jun. 23, 1994 now U.S. Pat. No 5,654,315, which is the national phase of International Application PCT/GB92/02333, filed Dec. 16, 1992 which designated the U.S. --.

Signed and Sealed this

Fourteenth Day of August, 2001

*Attest:*

NICHOLAS P. GODICI
*Attesting Officer*     Acting Director of the United States Patent and Trademark Office